(12) United States Patent  (10) Patent No.: US 7,736,902 B2
Inoue et al.  (45) Date of Patent: Jun. 15, 2010

(54) METHOD FOR DETERMINATION OF ABSOLUTE CONFIGURATION OF CHIRAL COMPOUNDS

(75) Inventors: Yoshihisa Inoue, Toyonaka (JP); Victor V. Borovkov, Toyonaka (JP); Guy A. Hembury, Leicester (GB)

(73) Assignee: Japan Science and Technology Agency, Saitama (JP)

( * ) Notice: Subject to any disclaimer, the term of this patent is extended or adjusted under 35 U.S.C. 154(b) by 1186 days.

(21) Appl. No.: 10/544,496

(22) PCT Filed: Feb. 6, 2004

(86) PCT No.: PCT/JP2004/001267

§ 371 (c)(1),
(2), (4) Date: Jan. 17, 2006

(87) PCT Pub. No.: WO2004/070364

PCT Pub. Date: Aug. 19, 2004

(65) Prior Publication Data

US 2006/0148091 A1    Jul. 6, 2006

(30) Foreign Application Priority Data

Feb. 6, 2003    (JP)  ............................. 2003-029190

(51) Int. Cl.
G01N 21/19    (2006.01)
G01N 33/00    (2006.01)
(52) U.S. Cl. ...................... 436/111; 436/112; 436/131; 436/164; 436/166; 436/171
(58) Field of Classification Search ................... 436/86, 436/89–98, 111–112, 131, 164, 166, 171
See application file for complete search history.

(56) References Cited

U.S. PATENT DOCUMENTS

| 5,493,017 | A  | * | 2/1996 | Therien et al. ............. 540/145 |
| 5,756,723 | A  | * | 5/1998 | Therien et al. ............. 540/145 |
| 7,354,771 | B2 | * | 4/2008 | Inoue et al. ................. 436/164 |
| 2003/0008406 | A1 | * | 1/2003 | Inoue et al. ................... 436/96 |
| 2005/0107604 | A1 | * | 5/2005 | Inoue et al. ................. 540/145 |
| 2006/0148091 | A1 | * | 7/2006 | Inoue et al. ................... 436/96 |

FOREIGN PATENT DOCUMENTS

JP    2-237939    9/1990

(Continued)

OTHER PUBLICATIONS

Kuroda, Y. et al, Journal of the American Chemical Society 1995, 117, 10950-10958.*

(Continued)

*Primary Examiner*—Arlen Soderquist
(74) *Attorney, Agent, or Firm*—Westerman, Hattori, Daniels & Adrian, LLP

(57) ABSTRACT

The present invention provides a simple, highly sensitive, and highly precise method for determining the absolute configuration of a chiral compound such as a diamine or an amino alcohol.

The present invention is directed to a method for determining the absolute configuration of an asymmetric carbon of a chiral compound on the basis of the sign of the Cotton effect by analyzing a solution containing the chiral compound and a porphyrin dimer by circular dichroism spectroscopy.

4 Claims, 5 Drawing Sheets

FOREIGN PATENT DOCUMENTS

| | | |
|---|---|---|
| JP | 6-58881 | 3/1994 |
| JP | 9-255682 | 9/1997 |
| JP | 11-2606 | 1/1999 |
| JP | 11-237375 | 8/1999 |
| JP | 2001-220392 | 8/2001 |
| JP | 2003-207444 | 7/2003 |
| JP | 2003-247933 | 9/2003 |
| WO | WO 01/40774 A1 | 6/2001 |

OTHER PUBLICATIONS

Furusho, Y. et al, Journal of the American Chemical Society 1997, 119, 5267-5268.*
Huang, X. et al, Chirality 2000, 12, 237-255.*
J. L. et al, Journal of the American Chemical Society 1987, 110, 3659-3661.*
Ohno, O. et al, Journal of Physical Chemistry 1987, 91, 4269-4273.*
Mizutani, T. et al, Inorganic Chemistry 1993, 32, 2072-2077.*
Johnson, D. G. et al, Journal of the American Chemical Society 1993, 115, 5692-5701.*
Mizutani, T. et al, Inorganic Chemistry 1994, 33, 3558-3566.*
Ema, T. et al, Tetrahedron Letters 1995, 36, 5905-5908.*
Matile, S. et al, Journal of the American Chemical Society 1996, 118, 5198-5206.*
Flores, V. et al, Tetrahedron Letters 1996, 8633-8636.*
Jensen, K. K. et al, Journal of Physical Chemistry A 1997, 101, 2218-2220.*
Tamiaki, H. et al, Tetrahedron Letters 1997, 38, 4239-4242.*
Mizutani, T. et al, Journal of the American Chemical Society 1997, 119, 8991-9001.*
Ogoshi, H. et al, Accounts of Chemical Research 1998, 31, 81-89.*
Rickman, B. H. et al, Tetrahedron 1998, 54, 5041-5064.*
Yang, S. I. et al, Journal of Physical Chemistry B 1998, 102, 9426-9436.*
Kilsa, K. et al, Journal of Physical Chemistry B 1999, 103, 7329-7339.*
Koehorst, R. B. M. et al, Journal of Physical Chemistry B 2000, 104, 2371-2377.*
Yoshida, N. et al, Tetrahedron Letters 2000, 41, 9287-9291.*
Cho, H. S. et al, Journal of Physical Chemistry A 2001, 105, 4200-4210.*
Aratani, N. et al, Organic Letters 2001, 3, 4213-4216.*
Yang, R. et al, Analytical Chemistry 2002, 74, 1088-1096.*
Berova et al., Exciton Chirality Method: Principles and Applications, 1994, 12, pp. 337-398.
University Science Books, Mill Valley, 1983, pp. 4-9.
Xuefei Huang, et al. Zinc Porphyrin Tweezer in Host-Guest Complexation: Determination of Absolute Configurations of Diamines, Amino Acids, and Amino Alcohols by Circular Dichroism, Journal American Chemical Society, 1998, 120, pp. 6185-6186.
Masayuki Takeuchi, et al. Molecular Design of Highly Selective and Sensitive "Sugar Tweezers" from Boronic Acid-Appended μ-Oxo-bis[porphinatoiron(III)]s, Bulletin of Chemical Society of Japan, 71, pp. 1117-1123, (1998).
Victor V. Borovkov, et al., "Synthesis of Zn-, Mn-, and Fe-Containing Mono- and Heterometallated Ethanediyl-Bridged Porphyrin Dimers", Helvetica Chimica Acta— vol. 82 (1999), pp. 919-934.
Victor V. Borovkov, et al., "Efficient Synthesis of Unsymmetrical Transition Metalloporphyrin Dimers under Mild Conditions", SYNLETT, pp. 768-770, (1998).
Rickman et al., A Two-Step Chemical/Chiroptical Method for Determining Absolute Configurations of α-Hydroxy Acids, Tetrahedron, 1998, 54, pp. 5041-5064.
Hayashi et al., Molecular Recognition of α, ω-Diamines by Metalloporphyrin Dimer, Tetrahedron Letters, vol. 38, No. 9, 1997, pp. 1603-1606.
Hai-Yang Liu et al. $^a$, Chiral linear assembly of amino acid bridged dimeric porphyrin hosts, Chem. Commun., 1997, pp. 1575-1576.
Takeuchi et al., Sugar-boronic acid interactions in the formation of novel chiral porphyrin dimers with various porphyrin-porphyrin angles, Chem. Commun., 1996, pp. 1867-1868.
Borovkov et al., Temperature Effect on Supramolecular Chirality Induction in Bis (zinc porphyrin)J. Am. Chem. Soc., 2000, 122, (18), pp. 4403-4407.
Sugiura et al., Interactions of Two Porphyrin Rings: Metal-Induced Structural Change of 5,5'-Ethylenebis (porphyrin), Bull. Chem. Soc. Jap., 1997, 70(5), pp. 1115-1123.
Higuchi et al., Synthesis and Properties of Tris (octaethylporphyrin)s Connected with Vinylene Groups, Bull. Chem. Soc. Jap., 1997, 70(8), pp. 1923-1933.
Borovkov et al., Supramolecular Chirality Induction in Bis (Zinc Porphyrin) by Amino Acid Derivatives: Rationalization and Applications of the Ligand Bulkiness Effect, Chirality, 2001, 13(6), pp. 329-335.
Borovkov et al., Supramolecular Chirogenesis in Zinc Porphyrins: Mechanism, Role of Guest Structure, and Application for the Absolute Configeration Determination, Journal of the American Chemical Society, 2001, 123(13), pp. 2979-2989.
Borovkov et al., Elucidation of the Mechanism of Superamolecular Chirality Inversion in Bis(zinc porphyrin) by Dynamic Approach Using CD and 1H NMR Spectroscopy, Journal of Physical Chemistry A, 2000, 104(40), pp. 9213-9219.
Higuchi et al., Synthesis and Structural and Electronic Properties of the Mixed Complexes of Vinylene-Bridged Bis- and Tris(octaethylporphyrin)s with Ni(II), Pd(II), and Pt(II) Ions, Bulletin of the Chemical Society of Japan, 2000, 73(5), pp. 1259-1275.
Borovkov et al., Supramolecular Chirogenesis in Bis(zinc porphyrin): An Absolute Configuration Probe Highly Sensitive to Guest Structure, Organic Letters, 2000, 2(11), pp. 1565-1568.
Higuchi et al., Synthesis and Electronic Properties of $d^8$ Transition-Metal Complexes of vinylene-Bridged Bis- and Tris(octaethylporphyrin)s, Bulletin of the Chemical Society of Japan, 1999, 72(8), pp. 1887-1898.

* cited by examiner $B_\parallel$:

Achiral

Chiral $B_\perp$:

Achiral

Chiral steric hindrance clockwise twist induced
by coordination of amine
of (s)-isomer

METHOD FOR DETERMINATION OF ABSOLUTE CONFIGURATION OF CHIRAL COMPOUNDS

FIELD OF THE INVENTION

The invention relates to a method for determining the absolute configuration of a chiral compound.

BACKGROUND ART

A method for determining the absolute configuration of a chiral compound that has been used in the past is to subject a combination (such as a complex) of a chiral compound and a specific compound to circular dichroic (CD) spectrophotometric analysis, and determine the absolute configuration of the chiral compound by utilizing the correlation between the Cotton effect sign and the absolute configuration of the chiral compound.

For instance, X. Huang et al. have reported that there is a correlation between the Cotton effect sign and the absolute configuration of a chiral compound, and that circular dichroism is induced by the coordination of a chiral compound to a porphyrin dimer that has been crosslinked with a long crosslinking chain (X. Huang, B. H. Rickmann, B. Borhan, N. Berova, K. Nakanishi, "Zinc Porphyrin Tweezer in Host-Guest Complexation: Determination of Absolute Configurations of Diamines, Amino Acids, and Amino Alcohols by Circular Dichroism," *J. Am. Chem. Soc.*, 1998, Vol. 120, pp. 6185-6186).

However, this system can only be applied to chiral compounds having two functional groups, such as a diamine or an amino alcohol, because circular dichroism is only induced by the simultaneous coordination of one molecule of chiral compound to two porphyrin units.

Also, M. Takeuchi et al. have reported that a porphyrin dimer having a phenylboronic acid unit exhibits circular dichroism in the presence of various kinds of sugar (M. Takeuchi, T. Imada, S. Shinkai, "Molecular Design of Highly Selective and Sensitive Sugar Tweezers from Boronic-Acid-Appended μ-Oxo-bis[porphinatoiron (III)]s," *Bull. Chem. Soc. Jpn.*, 1998, Vol. 71, 1117-1123).

This system can only be applied to sugars that form bonds with boronic acid. Furthermore, it is impossible to determine the absolute configuration of one specific asymmetric center out of the many asymmetric centers had by a sugar.

Thus, no method has been reported for determining absolute configuration which could be applied to a wide variety of chiral compounds.

In view of this, the inventors researched methods for determining the absolute configuration of a chiral compound with which the absolute configuration of many different chiral compounds could be determined precisely and easily. It has been discovered in recent years that when a chiral compound is coordinated to a metal porphyrin dimer which is a metal porphyrin dimer and in which both porphyrin rings include zinc, iron, manganese, or ruthenium as their metal center, circular dichroism is induced and there is a correlation between the Cotton effect sign and the absolute configuration of the chiral compound, and this has led to the completion of a novel method for determining the absolute configuration of a chiral compound (Japanese Unexamined Patent Publication 2001-220392).

Nevertheless, a problem with this method is that when the chiral compound is an amino alcohol or a diamine, the Cotton effect sign may be change with the concentration in which the chiral compound is contained in the sample solution.

SUMMARY OF THE INVENTION

The present invention was conceived in light of the problems encountered with prior art, and it is a primary object thereof to provide a method with which the absolute configuration of chiral compounds such as diamines and amino alcohols can be determined easily, at high sensitivity, and precisely.

As a result of diligent research, the inventors arrived at the present invention upon discovering that the stated object could be achieved by using a specific porphyrin dimer.

Specifically, the present invention relates to the following method for determining the absolute configuration of a chiral compound.

1. A method for determining the absolute configuration of an asymmetric carbon of a chiral compound on the basis of the sign of the Cotton effect by analyzing a solution containing the chiral compound and a porphyrin dimer by circular dichroism spectroscopy, wherein the porphyrin dimer:

(a) has a carbon chain-crosslinked porphyrin dimer structure, (b) is such that one porphyrin ring of the dimer has a metal center and the other porphyrin ring of the dimer is a free porphyrin ring, and (c) is such that the free porphyrin ring has a methyl group or substituent bulkier than a methyl group at one or more of the second carbons from the carbon bonded to the crosslinking carbon chain around the outer periphery of the free porphyrin ring, and the chiral compound:

(i) is capable of coordinating to the porphyrin dimer, and (ii) has an asymmetric carbon directly bonded to a group capable of coordinating to the porphyrin dimer, or an asymmetric carbon adjacent to the carbon atom bonded to a group capable of coordinating to the porphyrin dimmer.

2. The method according to above 1, wherein the porphyrin dimer is a compound represented by the following formula (1):

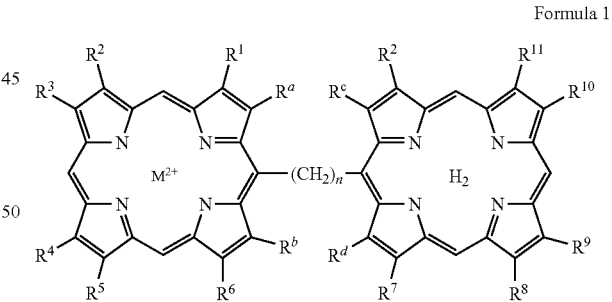

Formula 1 wherein $M^{2+}$ is a divalent metal ion selected from the group consisting of $Zn^{2+}$, an alkaline earth metal ion, and a transition metal ion, n is 2 or 3, $R^a$ to $R^d$ are the same or different and are each a hydrogen atom or a methyl group or substituent bulkier than a methyl group, either $R^c$ or $R^d$ is a bulky substituent at least as large as a methyl group, and $R^1$ to $R^{12}$ are the same or different and are each a hydrogen atom or a methyl group or substituent bulkier than a methyl group.

3. The method according to above 2, wherein either $R^c$ or $R^d$ in Formula 1 is selected from the group consisting of 1) a C1 to C8 hydrocarbon group, 2) an oxygen-containing substituent, 3) a nitrogen-containing substituent, 4) a halogen atom, and 5) a halogenated hydrocarbon group.

4. The method according to above 1, wherein the porphyrin dimer is a compound represented by the following formula (2):

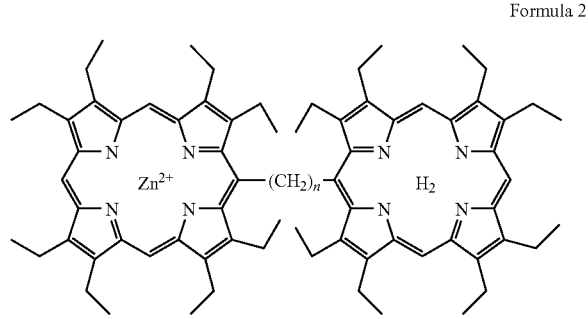

Formula 2

5. The method according to above 1, wherein said chiral compound is a compound selected from the group consisting of 1) a diamine, 2) a monoamine, 3) a monoalcohol, and 4) an amino alcohol.

BEST MODE FOR CARRYING OUT THE INVENTION

Figure 1:
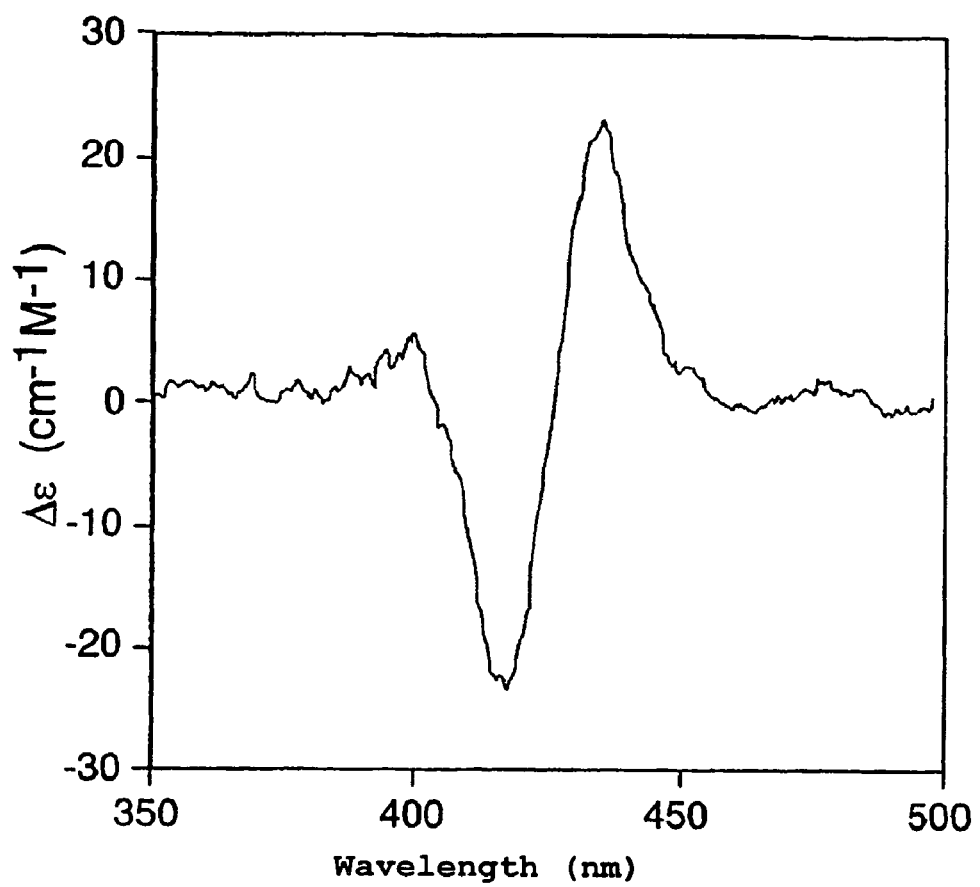
FIG. 1 is a graph of the results in Example 1, and shows the CD spectrum of a sample solution containing 1-(1-naphthyl) ethylamine.

The present invention relates to method for determining from the Cotton effect sign the absolute configuration of asymmetric carbons of a chiral compound having characteristics represented by the following (i) and (ii) by subjecting a solution containing the chiral compound and a porphyrin dimer having characteristics expressed by the following (a) to (c) to circular dichroic spectrophotometric analysis.

(a) A porphyrin dimer that has been crosslinked with a carbon chain, (b) is such that one porphyrin ring has a metal center and the other porphyrin ring is a free porphyrin ring, and (c) is a porphyrin dimer having a bulky substituent at least as large as a methyl group on at least one of the second carbons around the outer periphery of the porphyrin ring from the carbon bonded to the crosslinking carbon chain in the free porphyrin ring.

(i) A chiral compound that can be coordinated to the porphyrin dimer, and (ii) a chiral compound in which an asymmetric carbon is directly bonded to a group that can be coordinated to the porphyrin dimer, or a chiral compound in which one carbon atom is interposed between an asymmetric carbon and a group that can be coordinated to the porphyrin dimer.

There are no particular restrictions on the porphyrin dimer that can be used in the method of the present invention as long as it satisfies the above-mentioned requirements (a) to (c), but examples include compounds expressed by the following Formula 1.

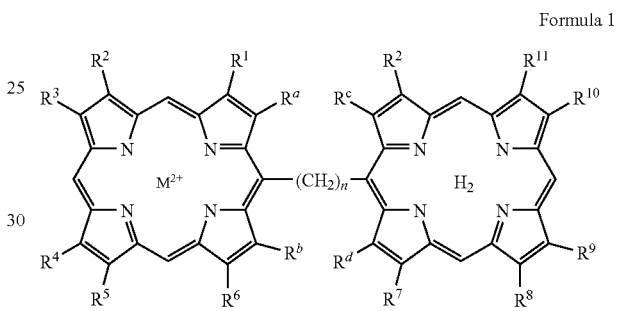

Formula 1

The requirements (a) to (c) will now be described while giving examples of compounds expressed by Formula 1.

Requirement (a)

Requirement (a) requires that the porphyrin dimer has been crosslinked with a carbon chain. Specifically, the porphyrin dimer used in the present invention comprises two porphyrin rings (porphyrin units) that have been crosslinked by a carbon chain. For example, in Formula 1, two porphyrin rings are crosslinked by $-(CH_2)_n-$.

There are no particular restrictions on the number of carbons in the crosslinking carbon chain, but it is usually about 2 or 3, and preferably 2. For instance, in Formula 1, n is 2 or 3, and preferably 2.

Requirement (b)

Requirement (b) requires that in the porphyrin dimer, one porphyrin ring has a metal center and the other porphyrin ring is a free porphyrin ring. For instance, in the compounds represented by Formula 1, the porphyrin ring on the left has $M^{2+}$ as a metal center. Meanwhile, since the porphyrin ring on the right is free, it has two hydrogen atoms in the center.

Examples of central metals include divalent metal ions such as $Zn^{2+}$, alkaline earth metal ions, and transition metal ions. Examples of alkaline earth metal ions include $Mg^{2+}$, $Ca^{2+}$, $Sr^{2+}$, and $Ba^{2+}$. Examples of transition metal ions include $Fe^{2+}$, $Ru^{2+}$, and $Mn^{2+}$. The central metal is preferably $Zn^{2+}$ or $Mg^{2+}$, with $Zn^{2+}$ being particularly favorable.

Examples of $M^{2+}$ in Formula 1 include divalent metal ions such as $Zn^{2+}$, alkaline earth metal ions, and transition metal ions, of which $Zn^{2+}$ or $Mg^{2+}$ are preferable, with $Zn^{2+}$ being particularly favorable.

Requirement (c)

Requirement (c) requires that the free porphyrin ring dimer in the porphyrin dimer has a bulky substituent at least as large as a methyl group on at least one of the second carbons around the outer periphery of the porphyrin ring from the carbon bonded to the crosslinking carbon chain. For instance, with the compounds represented by Formula 1, $R^c$ and $R^d$ are substituents bonded to the second carbons around the outer periphery of the porphyrin ring from the carbon bonded to the crosslinking carbon chain in the free porphyrin ring. Therefore, in the case of the compounds represented by Formula 1, Requirement (c) is met if either $R^c$ or $R^d$ is a bulky substituent at least as large as a methyl group.

In Formula 1, $R^a$ to $R^d$ are the same or different and are each a hydrogen atom or a bulky substituent at least as large as a methyl group, and either $R^c$ or $R^d$ is a bulky substituent at least as large as a methyl group.

In Formula 1, $R^1$ to $R^{12}$ are the same or different and are each a hydrogen atom or a bulky substituent at least as large as a methyl group.

The phrase "bulky substituent at least as large as a methyl group" means a substituent whose bulk is the same as or greater than that of a methyl group. Examples of bulky substituents at least as large as a methyl group include 1) C1 to C8 hydrocarbon groups, 2) oxygen-containing substituents, 3) nitrogen-containing substituents, 4) halogen atoms, and 5) halogenated hydrocarbon groups. Of the above 1 to 5, a C1 to C8 hydrocarbon group (1) is preferable.

Examples of C1 to C8 hydrocarbon groups include a methyl group, ethyl group, propyl group, n-butyl group, isobutyl group, and other such linear and branched alkyl groups. The carbon number of this hydrocarbon group is usually about 1 to 10, and preferably about 1 to 8, and even more preferably about 1 to 4.

Examples of oxygen-containing substituents (2) include ester groups and carboxyalkyl groups. Examples of ester groups include a methyl ester group, ethyl ester group, and other such alkyl ester groups. Examples of carboxyalkyl groups include a carboxymethyl group. The carbon number of the alkyl portion of the alkyl ester group and the alkyl portion of the carboxyalkyl group is usually about 1 to 10, and preferably about 1 to 5.

Examples of nitrogen-containing substituents (3) include an amino group, amide group, and 2-aminoethyl group.

Examples of halogen atoms (4) include chlorine, bromine, and fluorine.

Examples of halogenated hydrocarbon groups (5) include a chloromethyl group, chloroethyl group, chloropropyl group, and chlorobutyl group. The carbon number of the halogenated hydrocarbon group is usually about 1 to 10, and preferably about 1 to 5. There are no particular restrictions on the number of halogen atoms included in the halogenated hydrocarbon group, but the number is usually about 1 to 23, and preferably about 1 to 9.

In the present invention, it is preferable, for example, to use a porphyrin dimer in which $R^1$ to $R^{12}$ and $R^a$ and $R^b$ are all the same bulky substituent at least as large as a methyl group. An example of such a porphyrin dimer is the compound represented by the following Formula 2: zinc [[5,5'-(ethan-1,2-diyl)bis[2,3,7,8,12,13,17,18-octaethyl-21H,23H-porphyrinate](2-)]-κN$^{21}$, κN$^{22}$,κN$^{23}$,κN$^{24}$]]. The compound expressed by Formula 2 will hereinafter be referred to as "Compound 1."

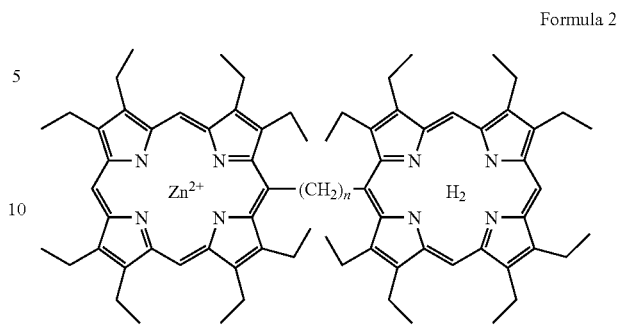

Formula 2

There are no particular restrictions on the method for manufacturing the porphyrin dimer used in the present invention, and this dimer can be prepared by a known method. One example is the method discussed in V. V. Borovkov, J. M. Lintuluoto, and Y. Inoue, *Helv. Chem. Acta,* 1999, 82, 919-934, in V. V. Borovkov, J. M. Lintuluoto, and Y. Inoue, *Synlett,* 1998, 768, and elsewhere. More specifically, this dimer can be manufactured, for example, by a method in which a porphyrin dimer in which no metal center has been introduced (hereinafter referred to as the "free porphyrin dimer") is reacted with a carboxylate, halide, or the like of the desired central metal to introduce the central metal into one of the porphyrin rings of the free porphyrin dimer. The porphyrin dimer thus obtained may be refined as needed by a known method. An example of a carboxylate of a central metal is $Zn(CH_3COO)_2$. Examples of halides include halides of zinc, and $MgBr_2.Et_2O$ and other such halides of alkaline earth metals.

If a solution containing the above-mentioned porphyrin dimer and a chiral compound having the following characteristics (i) and (ii) is subjected to circular dichroic spectrophotometric analysis, the absolute configuration of the asymmetric carbons of the chiral compound can be determined from the sign of the Cotton effect.

(i) A chiral compound that can be coordinated to the porphyrin dimer, and (ii) a chiral compound in which an asymmetric carbon is directly bonded to a group that can be coordinated to the porphyrin dimer, or a chiral compound in which one carbon atom is interposed between an asymmetric carbon and a group that can be coordinated to the porphyrin dimer.

A chiral compound whose absolute configuration can be determined by the method of the present invention is a compound that can be coordinated to the above-mentioned porphyrin dimer, that is, a compound that can form a complex with the porphyrin dimer. For example, it is a compound having an amino group, hydroxyl group, or other such basic group as a group that can be coordinated to a porphyrin dimer. Specific examples include 1) diamines, 2) primary monoamines, secondary monoamines, and other such monoamines, 3) monoalcohols, and 4) amino alcohols.

Examples of diamines include 1,2-diaminocyclohexane and 1,2-diamino-1,2-diphenylethane.

Examples of primary monoamines include 2-butylamine, 1-(1-phenyl)ethylamine, 1-(1-naphthyl)ethylamine, 1-cyclohexylethylamine, 2-methyl-1-butylamine, [endo-(1R)-1,7,7-trimethylbicyclo[2,2,1]heptane-2-amine], 1-bornylamine, valine methyl ester, and isopinocampheol.

Examples of secondary monoamines include N-methyl-1-phenylethylamine.

Examples of amino alcohols include 1-amino-2-propanol, 2-amino-4-methyl-1-pentanol, and threonine methyl ester.

Examples of monoalcohols include borneol, 2-butanol, 1-phenylethanol, and menthol.

A chiral compound whose absolute configuration can be determined by the method of the present invention is a chiral compound in which an asymmetric carbon is bonded to a group that can be coordinated to the central metal had by one of the porphyrin rings of the porphyrin dimer, or a chiral compound in which one carbon atom is interposed between an asymmetric carbon and the group that can be coordinated. For example, 2-butanol, 1-phenylethanol, 1-phenylethylamine, and the like correspond to chiral compounds in which an asymmetric carbon is directly bonded to a group that can be coordinated to the central metal of the porphyrin dimer.

When the chiral compound has two or more groups that can be coordinated to a porphyrin dimer, such as a diamine or an amino alcohol, it is possible to determine the absolute configuration of the asymmetric carbon to which is bonded the group actually coordinated to the metal center of the porphyrin, or the asymmetric carbon bonded via one carbon atom to the coordinated group. With an amino alcohol, for example, since an amino group generally coordinates readily to a porphyrin dimer, the absolute configuration can usually be determined for an asymmetric carbon directly bonded to the amino group, or an asymmetric carbon where a carbon atom is interposed between the asymmetric carbon and the amino group.

When a chiral compound having a plurality of asymmetric carbons is used, it is possible to determine the absolute configuration for asymmetric carbons directly bonded to a group that can be coordinated to the metal center of the porphyrin dimer, or asymmetric carbons bonded via one carbon atom to the coordinating group. For example, in the case of bornylamine, out of the two asymmetric carbon atoms, it is possible to determine the absolute configuration of the one to which the amino group is bonded.

The sample solution used in circular dichroic spectrophotometric analysis contains the above-mentioned porphyrin dimer and chiral compound. The sample solution may also contain other added components as long as the desired effect is still obtained.

There are no particular restrictions on the method for preparing the sample solution, but it can be prepared, for example, by a method in which the porphyrin dimer, chiral compound, and so forth are dissolved in a solvent.

The solvent used to prepare the sample solution is preferably one that will not coordinate to a porphyrin dimer. Examples of solvents that will not coordinate to a porphyrin dimer include chloroform ($CHCl_3$), dichloromethane ($CH_2Cl_2$), dichloroethane ($CH_2ClCH_2Cl$), tetrachloroethane ($CHCl_2CHCl_2$), tetrachloromethane ($CCl_4$) and other such halogenated aliphatic hydrocarbons, and hexane, heptane, and other such aliphatic hydrocarbons.

There are no particular restrictions on the concentrations of the chiral compound and porphyrin dimer in the sample solution. The circular dichroism spectrum (CD spectrum) of the sample solution usually exhibits two peaks, namely, one maximum value and one minimum value. Hereinafter, the peak on the longer wavelength side will sometimes be referred to as the "first Cotton effect," and the peak on the shorter wavelength side as the "second Cotton effect." There are no particular restrictions on the lower limits to the chiral compound and porphyrin dimer in the sample solution, as long as the first or second Cotton effect can be detected, and these limits can be suitably set according to the type of porphyrin dimer being used, the type of chiral compound, the type of solvent, and so forth. The upper limit of the concentration of chiral compound in the sample solution and the upper limit of the concentration of porphyrin dimer are preferably set such that, for example, the ellipticity of the first or second Cotton effect in the circular dichroism spectrum is about twice the noise level or greater (such as about 1 mdeg or higher), the voltage of a photomultiplier tube is −700 kV or less, and the ellipticity of the first or second Cotton effect is as high as possible. It is even more preferable for the setting to be such that the ellipticity of the first or second Cotton effect is about 10 to 50 mdeg.

The concentration of the chiral compound in the sample solution can be suitably set as dictated by the type of chiral compound and other such factors, but is usually at least about $10^{-5}$ mol/L, and preferably about $10^{-5}$ to $10^{-1}$ mol/L, and even more preferably about $10^{-4}$ to $10^{-3}$ mol/L.

The concentration of the porphyrin dimer in the sample solution can be suitably set as dictated by the type of chiral compound and other such factors, but is usually at least about $10^{-7}$ mol/L, and preferably at least about $10^{-6}$. There are no particular restrictions on the upper limit of the concentration of porphyrin dimer in the sample solution, which can be suitably set according to the type of chiral compound and so forth, but it is usually no more than about $10^{-4}$ mol/L, and preferably no more than about $10^{-5}$ mol/L.

There are no particular restrictions on the temperature at which the dichroic spectrophotometric analysis is performed, as long as the Cotton effect can be detected, but the temperature is usually about −80 to +30° C. Normally, the lower the temperature, the higher the sensitivity at which the analysis can be performed.

In the CD spectrum of the sample solution, the sign of the first Cotton effect and second Cotton effect may be either positive or negative, and the sign of the first Cotton effect is opposite to the sign of the second Cotton effect. For instance, to use the CD spectrum of the (S)-1-(1-naphthyl)ethylamine shown in FIG. 1 as an example, the sign of the first Cotton effect is positive (plus), while the sign of the second Cotton effect is negative (minus). When the chiral compound comes in different optical isomers (such as R-isomers and S-isomers), the respective signs of the Cotton effects will be opposite. For example, when (R)-1-(1-naphthyl)ethylamine is used, the sign as opposite those in FIG. 1, with the sign of the first Cotton effect being negative, and the sign of the second Cotton effect positive. The sign of either peak may be used to determine the absolute configuration, but the first Cotton effect can be used more favorably because it is easier to detect.

The CD spectrum was measured for a sample solution containing the reagent of the present invention and various chiral compounds of known absolute configuration in order to demonstrate that there is a specific correlation between the signs of the Cotton effects in a sample solution and the absolute configuration (either R-isomer or S-isomer) of the asymmetric carbons of a chiral compound. Table 1 below shows the signs of the Cotton effects in the sample solution and the absolute configurations of various chiral compounds. The porphyrin represented by Formula 2 below (Compound 1) was used as the porphyrin dimer, and its concentration in the sample solution was set at $10^{-6}$ mol/L. Methylene chloride was used as the solvent. The concentrations of the various chiral compounds in the sample solution are given in Table 1.

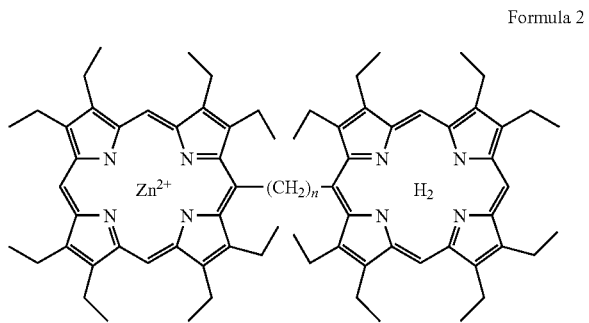

Formula 2

TABLE 1

| Chiral compound (conc.: ×10$^{-2}$ mol/L) | Absolute configuration and sign of chiral compound | Sign of second Cotton effect (B$_\perp$ transition) | Sign of first Cotton effect (B$_\parallel$ transition) |
|---|---|---|---|
| 1-(1-naphthyl)ethylamine (4.1) | (R)-(+) | + | − |
| | (S)-(−) | − | + |
| 1-(1-phenyl)ethylamine (5.2) | (R)-(+) | + | − |
| | (S)-(−) | − | + |
| 1-cyclohexylethylamine (4.5) | (R)-(+) | + | − |
| | (S)-(−) | − | + |
| 1-bornylamine (6.1)*[1] | (1R,2S) | − | + |
| 1,2-diaminocyclohexane (5.8) | (1R,2R)-(−) | + | − |
| | (1S,2S)-(+) | − | + |
| valine methyl ester (16.3) | (S)-(+) | − | + |

*[1]An amino group bonded to the carbon at the 2S position is what is coordinated to the porphyrin dimer As is clear from Table 1, there is a specific correlation between the sign of the Cotton effect and the steric configuration of the asymmetric carbon in the alpha or beta position of an amino group or other such coordinatable group. Specifically, when the sign of the first Cotton effect is positive, the absolute configuration of the asymmetric carbon at the alpha or beta position is (S). On the other hand, when the sign of the first Cotton effect is negative, the absolute configuration of the asymmetric carbon at the alpha or beta position is (R). This correlation and the sign of the Cotton effect of an unknown sample solution can be utilized to determine the absolute configuration for a chiral compound in an unknown sample solution.

Figure 2:
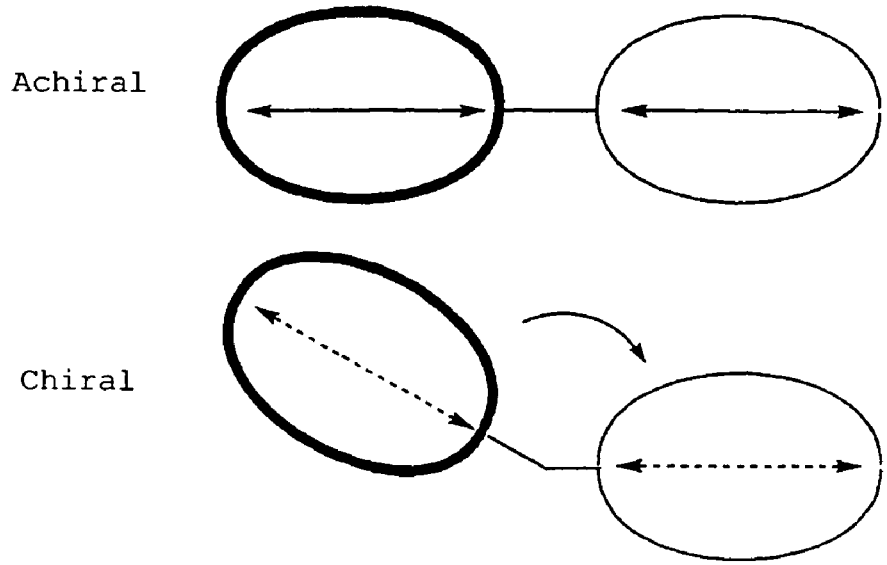
FIG. 2 is a diagram illustrating the direction of moment related to the B band, which is the maximum absorption band of the porphyrin dimer (in FIG. 2, the porphyrin dimer is depicted in simplified fashion, with the porphyrin ring shown as an ellipse and the crosslinking carbon chain as a straight line, the two ellipses (porphyrin rings) do not lie in the same plane, and are located one above the other, with the ellipse that is actually above drawn with a thicker line in order to illustrate the upper and lower spatial relationship of the two ellipses, and the chiral structure has clockwise chirality)
Figure 2:
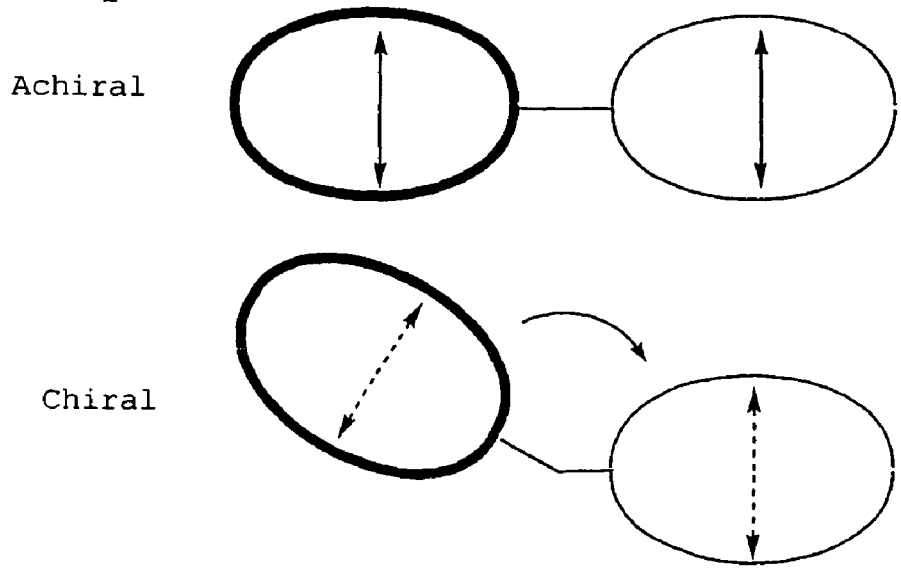

"B$_\parallel$ transition" in Table 1 is the transition when the transition moments of the two porphyrin rings at which the absorption band is the B band (Soret band) are both in the direction of bonding the porphyrin rings, while "B$_\perp$ transition" is the transition when the above-mentioned transition moments are both perpendicular to the direction of bonding the porphyrin rings. In FIG. 2, the solid lines indicate the direction of the transition moment of an achiral porphyrin dimer prior to the coordination of the chiral compound.

Meanwhile, with a porphyrin dimer in which the chiral compound has been coordinated, as indicated by the dotted lines in FIG. 2, regardless of whether the transition is B$_\parallel$ or B$_\perp$, the direction of the transition moment of one ring is slightly shifted with respect to the direction of the other transition moment as compared to an achiral porphyrin dimer.

The mechanism by which an induced Cotton effect is produced in the present invention will now be described. When a solution containing a porphyrin dimer and the above-mentioned chiral compound is prepared, the chiral compound is coordinated to the metal center of the porphyrin dimer. Along with this coordination of the chiral compound, the porphyrin dimer exhibits a conformation change from a syn-type to an anti-type, and at the same time, asymmetry is induced in the anti-type conformer, and the circular dichroism shown in FIG. 1 is exhibited.

Figure 3:
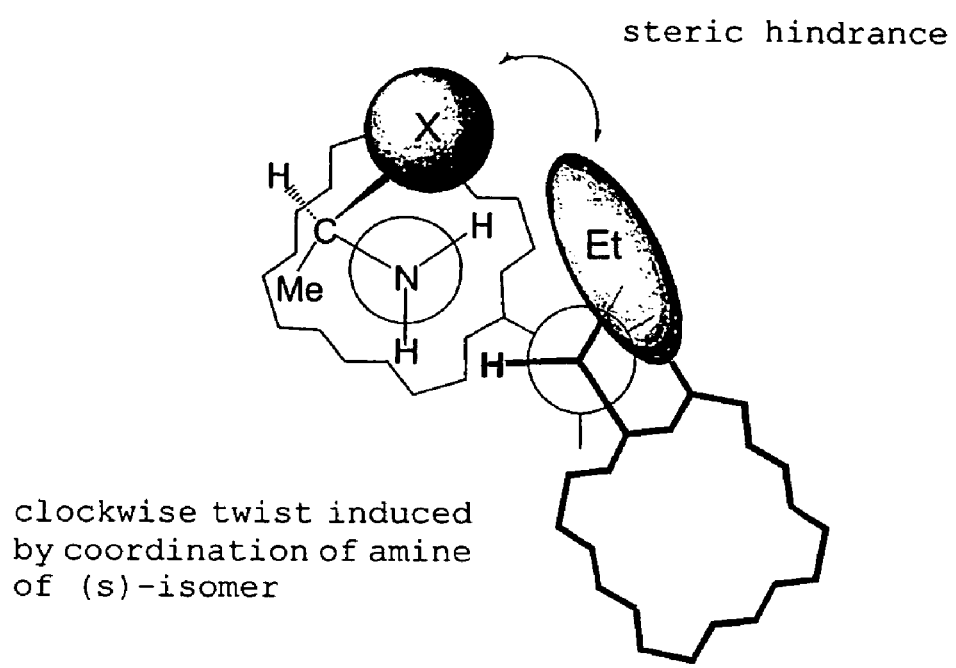
FIG. 3 is a schematic diagram of the mechanism for asymmetric inducement in the porphyrin dimer (in FIG. 3, the upper porphyrin ring (the free porphyrin ring) out of the two porphyrin rings is drawn with a thicker line)

The mechanism of asymmetry induction is described by twisting of the porphyrin rings as shown in FIG. 3. FIG. 3 illustrates the case when an S-isomer amine was used as the chiral compound. Steric hindrance occurs between the largest substituent (X) bonded to the alpha or beta carbon (the alpha carbon in FIG. 3) of the chiral compound (ligand) and a bulky substituent at least as large as a methyl group that is bonded to the porphyrin ring to which the chiral compound is not coordinated (free porphyrin ring), thereby producing a twist in the configuration of the porphyrin, and it can be understood that circular dichroism appears on the basis of exciton interaction between the porphyrins.

According to the CD exciton chirality method, when two electron transition moments that act on each other are arranged clockwise from front to back, positive chirality is created, but when the arrangement is counterclockwise, negative chirality is created (N. Harada, K. Nakanishi, "Circular Dichroic Spectroscopy-Exciton Coupling in Organic Stereochemistry," University Science Books, Mill Valley, 1983; K. Nakanishi, N. Berova, "In Circular Dichroism: Principles and Applications," R. Woody, Ed., VCH Publishers, New York, 1994, pp. 361-398).

For example, when a chiral compound whose absolute configuration is S is coordinated to a porphyrin dimer, it is twisted clockwise from front to back (see FIG. 3), and the sign of the first Cotton effect is "positive." On the other hand, when a chiral compound whose absolute configuration is R is coordinated to a porphyrin dimer, it is twisted counterclockwise from front to back, and the sign of the first Cotton effect is "negative."

With the method of the present invention, circular dichroic (CD) spectrophotometric analysis is used to analyze a sample solution containing a chiral compound, a porphyrin dimer, etc. Specifically, with the method of the present invention, the absolute configuration of the chiral compound can be determined from the sign of the Cotton effect of the CD spectrum obtained when the chiral compound to be measured has been coordinated to a porphyrin dimer.

EXAMPLES

Examples of the present invention will now be given along with comparative examples to describe the present invention in more specific terms. The present invention is not, however, limited to the following working examples.

A Jasco J-720WI spectropolarimeter was used to measure the CD spectrum.

Manufacturing Example 1

A porphyrin dimer containing a metal center in one porphyrin ring was manufactured as depicted in the following scheme.

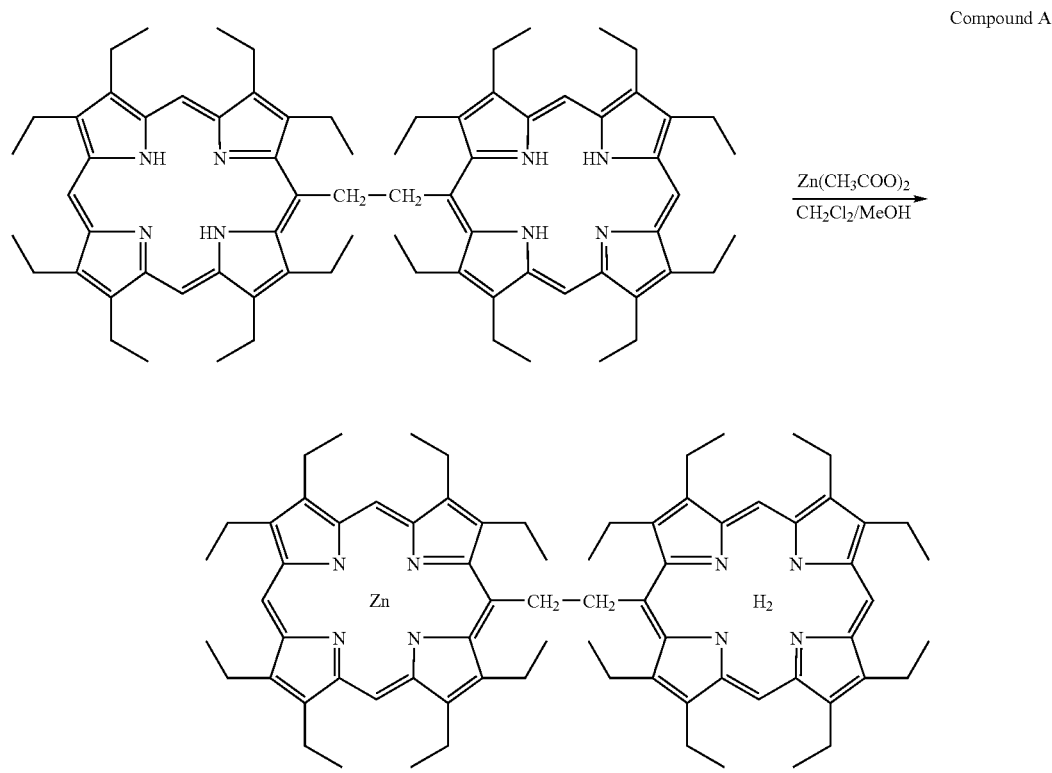

Compound A

A CH$_2$Cl$_2$ solution of a free porphyrin dimer (Compound A) was refluxed, and a methanol solution of Zn(CH$_3$COO)$_2$ was added dropwise to this refluxed solution. The amount of Zn(CH$_3$COO)$_2$ was 1.2 equivalents versus Compound A. The reaction mixture thus obtained was refined by chromatography (filler: silica gel, eluant: CHCl$_3$). The yield was 60%.

Example 1

A 3 mL (optical wavelength: 1 cm) cell was used to measure the CD spectrum at 25° C. for a CH$_2$Cl$_2$ solution containing approximately 10$^{-6}$ mol/L Compound 1 and 4.1×10$^{-2}$ mol/L (S)-1-(1-naphthyl)ethylamine. The results are given in FIG. 1.

As is clear from FIG. 1, the sign of the first Cotton effect on the long wavelength side was positive. The absolute configuration of the carbon directly bonded to the amino group of the 1-(1-naphthyl)ethylamine was confirmed to be S.

Example 2

A 3 mL (optical wavelength: 1 cm) cell was used to measure the ultraviolet-visible absorption spectrum and the CD spectrum at 25° C. for a CH$_2$Cl$_2$ solution containing Compound 1 (5.41×10$^{-6}$ mol/L) and various concentrations of L-threonine methyl ester. The threonine methyl ester had two asymmetric carbons. The L-threonine methyl ester used in Working Example 2 and Comparative Example 1 was such that the absolute configuration of the asymmetric carbon bonded to the amino group was S, and the absolute configuration of the other carbon was R.

Figure 4:
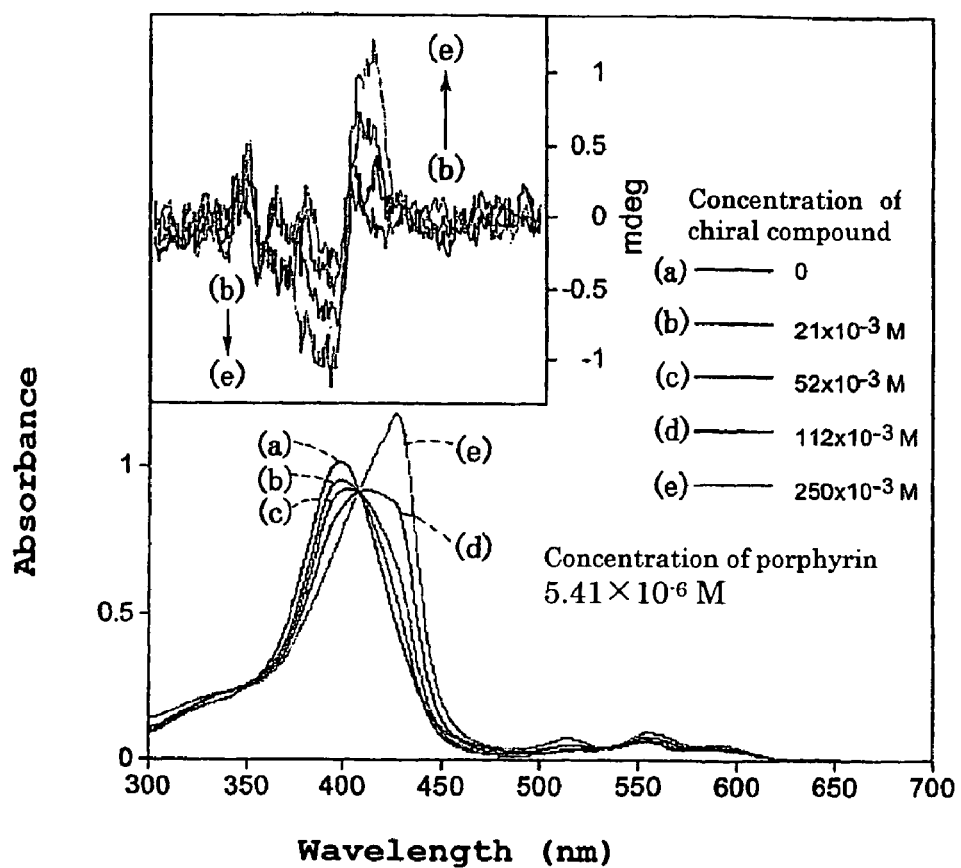
FIG. 4 is a graph of the CD spectrum and the ultraviolet-visible absorption spectrum, which show the results of Example 2 (the upper-left graph is the CD spectrum)

The results are given in FIG. 4. The ultraviolet-visible absorption spectrum was also measured for a CH$_2$Cl$_2$ solution containing just Compound 1. Table 2 below shows the sign of the Cotton effect for the various concentrations.

TABLE 2

| Chiral compound concentration (mol/L) | Sign of second Cotton effect | Sign of first Cotton effect |
|---|---|---|
| 21 × 10$^{-3}$ | not detected | not detected |
| 52 × 10$^{-3}$ | − | + |
| 112 × 10$^{-3}$ | − | + |
| 250 × 10$^{-3}$ | − | + |

At all concentrations, the first Cotton effect was positive and the second Cotton effect was negative. The amino group of the threonine methyl ester was coordinated to Compound 1. Therefore, these results are consistent with the absolute configuration of the asymmetric carbon directly bonded to the amino group of the triennia methyl ester being S.

Comparative Example 1

A 3 mL (optical wavelength: 1 cm) cell was used to measure the ultraviolet-visible absorption spectrum and the CD spectrum at 25° C. for a CH$_2$Cl$_2$ solution containing a dizinc porphyrin dimer represented by the following formula (Compound B, 5.76×10$^{-6}$ mol/L) and various concentrations of L-threonine methyl ester. The results are given in FIG. 5. The ultraviolet-visible absorption spectrum was also measured for a CH$_2$Cl$_2$ solution containing just Compound B. Table 3 below shows the sign of the Cotton effect for the various concentrations.

TABLE 3

| Chiral compound concentration (mol/L) | Sign of second Cotton effect | Sign of first Cotton effect |
|---|---|---|
| 20 × 10$^{-3}$ | − | + |
| 53 × 10$^{-3}$ | − | + |
| 134 × 10$^{-3}$ | − | + |
| 232 × 10$^{-3}$ | + | − |

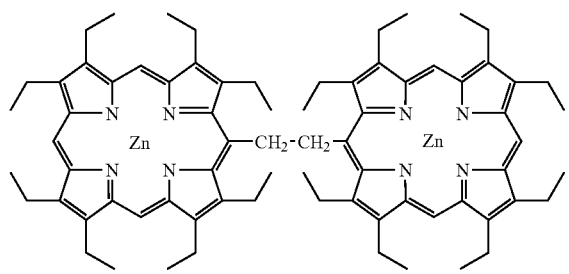

dizinc {μ-{{5,5'-(ethan-1,2-diyl)bis[2,3,7,8,12,13,17,18-octaethyl-21H,23H-porphyrinate](4-)}-κN$^{21}$, κN$^{22}$,κN$^{23}$, κN$^{24}$:κN$^{21'}$,κN$^{22'}$,κN$^{23'}$,κN$^{24'}$}}

Figure 5:
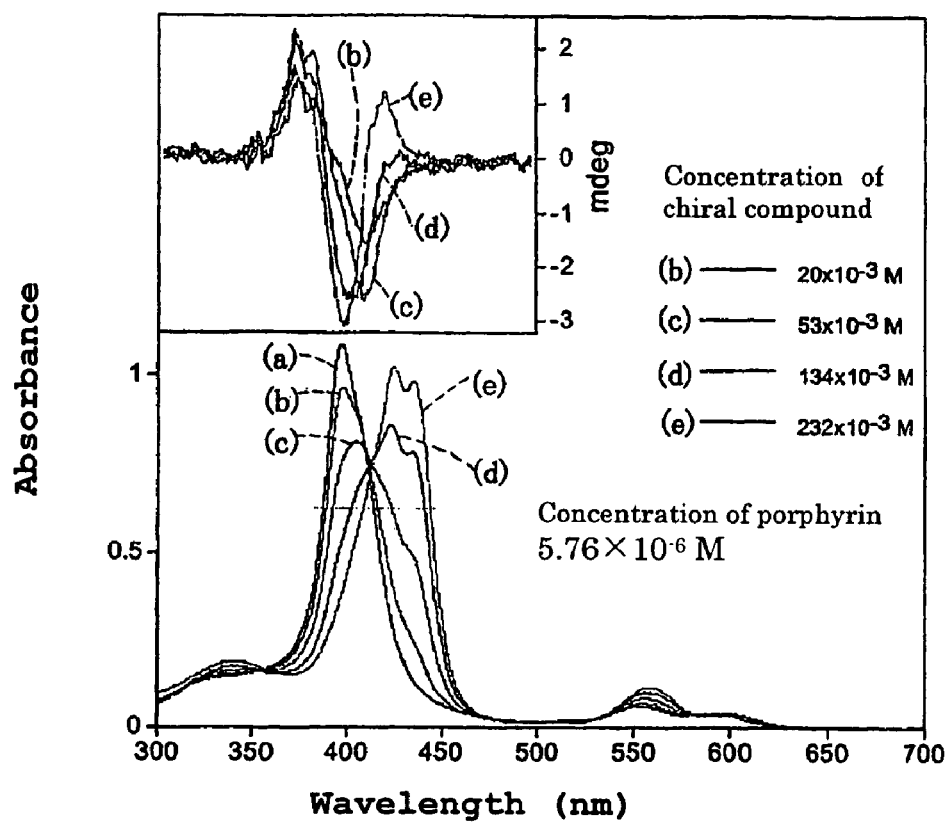
FIG. 5 is a graph of the CD spectrum and the ultraviolet-visible absorption spectrum, which show the results of Comparative Example 1 (the upper-left graph is the CD spectrum).

As is clear from Table 3 and the upper-left graph in FIG. 5, as the concentration of the L-threonine methyl ester (the chiral compound) rose, the sign of the Cotton effect reversed. Specifically, when the concentration of chiral compound was low, the sign of the first Cotton effect was negative, but when the concentration of chiral compound was high, the sign reversed to positive.

When the concentration of amino alcohol with respect to the dizinc porphyrin dimer is low, the dizinc porphyrin dimer and the amino alcohol form a 1:1 complex. When the concentration of amino alcohol with respect to the dizinc porphyrin dimer becomes high, though, the porphyrin dimer and the amino alcohol may form a 1:2 complex, with the sign of the Cotton effect being opposite that with a 1:1 complex. When the concentrations of dizinc porphyrin dimer and amino alcohol are set so that the dizinc porphyrin dimer and amino alcohol will form a 1:1 complex, the absolute configuration of the amino alcohol can be determined even when a dizinc porphyrin dimer is used.

The hydroxyl group of the threonine methyl ester is coordinated to Compound B. Therefore, it can be seen from the results of Comparative Example 1 that the absolute configuration of the asymmetric carbon directly bonded to the hydroxyl group of the threonine methyl ester is R.

Also, when a diamine is used as the chiral compound, just as with an amino alcohol, if the sample solution is prepared such that the dizinc porphyrin dimer and the diamine form a 1:1 complex, the absolute configuration of the diamine can be determined using a dizinc porphyrin dimer.

INDUSTRIAL APPLICABILITY

According to the present invention, the absolute configuration of asymmetric carbons can be determined for a chiral compound, and particularly a diamine, amino alcohol, or other such chiral compound, regardless of the concentration of the chiral compound.

With the present invention, the absolute configuration of asymmetric carbons can be determined for a chiral compound which can be coordinated to a porphyrin dimer, in which an asymmetric carbon is directly bonded to a group that can be coordinated to the porphyrin dimer, or in which one carbon atom is interposed between an asymmetric carbon and a group that can be coordinated to the porphyrin dimer.

With the present invention, there is no need to introduce special modifying groups into the chiral compound during measurement. This means that the chiral compound can be easily recovered as needed. For example, if a hydrochloric acid aqueous solution of about 2 mol/L and the measured sample solution are stirred, a complex composed of a porphyrin dimer and a chiral compound will decompose into a hydrochloride of the chiral compound (such as a chiral amine hydrochloride) and a free porphyrin dimer, so the chiral compound can be separated and recovered. The separated and recovered free porphyrin dimer can be reused by introducing a central metal ion once again.

With the present invention, the absolute configuration of a chiral compound can be determined extremely rapidly. The time it takes to prepare the sample and to measure the CD spectrum will vary with the conditions, but is no more than 10 minutes.

The absorption of most chiral compounds is 400 nm or less. With the method of the present invention, meanwhile, the Cotton effect can be detected at a longer wavelength, such as about 400 to 450 nm. Specifically, the peak at which the Cotton effect is exhibited can be detected at a wavelength that does not overlap the peak exhibited by the chiral compound itself. Therefore, with the present invention, it is possible to determine the absolute configuration for an extremely broad range of chiral compounds.

X-ray diffraction is a conventional method for determining the absolute configuration of a chiral compound, but this method can only be applied to crystalline compounds. With the present invention, the absolute configuration can be determined whether or not the chiral compound is crystalline.

The invention claimed is:

1. A method for determining the absolute configuration of an asymmetric carbon of a chiral compound on the basis of the sign of the Cotton effect by analyzing a solution containing the chiral compound and a porphyrin dimer by circular dichroism spectroscopy, wherein the porphyrin dimer:
   (a) has a carbon chain-crosslinked porphyrin dimer structure,
   (b) is such that one porphyrin ring of the dimer has a Zn$^{2+}$ metal center and the other porphyrin ring of the dimer is a free porphyrin ring, and
   (c) is such that the free porphyrin ring has a methyl group or substituent bulkier than a methyl group at one or more of the second carbons from the carbon bonded to the crosslinking carbon chain around the outer periphery of the free porphyrin ring, and the chiral compound:
   (i) is capable of coordinating to the porphyrin dimer,
   (ii) has an asymmetric carbon directly bonded to a group capable of coordinating to the porphyrin dimer, or an asymmetric carbon adjacent to the carbon atom bonded to a group capable of coordinating to the porphyrin dimer, and
   (iii) is a diamine or an amino alcohol.

2. The method according to claim 1, wherein the porphyrin dimer is a compound represented by the following formula (1):

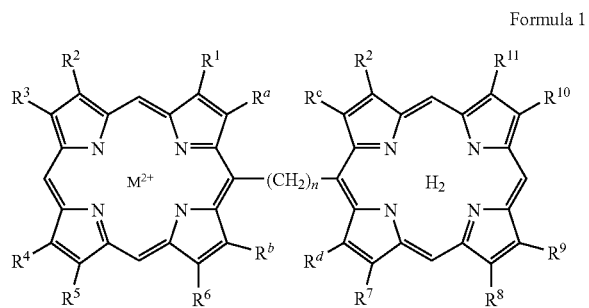

Formula 1

Formula 1
wherein $M^{2+}$ is $Zn^{2+}$,
n is 2 or 3,
$R^a$ to $R^d$ are the same or different and are each a hydrogen atom or a methyl group or substituent bulkier than a methyl group,
either $R^c$ or $R^d$ is a methyl group or substituent bulkier than a methyl group, and
$R^1$ to $R^{12}$ are the same or different and are each a hydrogen atom or a methyl group or substituent bulkier than a methyl group.

3. The method according to claim 2, wherein either $R^c$ or $R^d$ in Formula 1 is selected from the group consisting of 1) a C1 to C8 hydrocarbon group, 2) an oxygen-containing substituent, 3) a nitrogen-containing substituent, 4) a halogen atom, and 5) a halogenated hydrocarbon group.

4. The method according to claim 1, wherein the porphyrin dimer is a compound represented by the following formula (2):

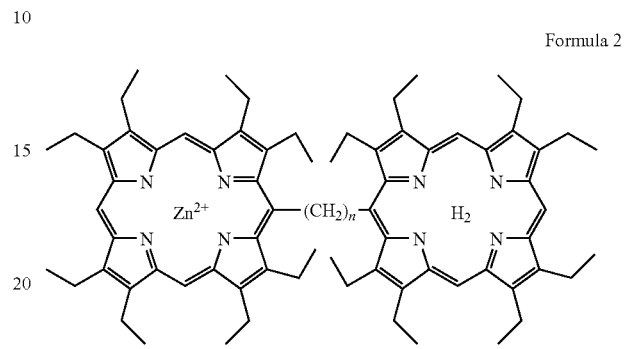

Formula 2

Formula 2.

* * * * *